US008524676B2

(12) United States Patent
Stein et al.

(10) Patent No.: US 8,524,676 B2
(45) Date of Patent: *Sep. 3, 2013

(54) METHOD FOR TREATING ENTEROVIRUS OR RHINOVIRUS INFECTION USING ANTISENSE ANTIVIRAL COMPOUNDS

(75) Inventors: David A. Stein, Corvallis, OR (US); Richard K. Bestwick, Corvallis, OR (US); Patrick L. Iversen, Corvallis, OR (US); Dwight D. Weller, Corvallis, OR (US)

(73) Assignee: Sarepta Therapeutics, Inc., Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/517,757

(22) Filed: Sep. 8, 2006

(65) Prior Publication Data

US 2007/0066556 A1    Mar. 22, 2007

Related U.S. Application Data

(60) Provisional application No. 60/716,001, filed on Sep. 8, 2005, provisional application No. 60/800,145, filed on May 11, 2006.

(51) Int. Cl.
*C12N 15/11*    (2006.01)
*A61K 38/00*    (2006.01)
*C07H 21/04*    (2006.01)

(52) U.S. Cl.
CPC ..................................... *A61K 38/00* (2013.01)
USPC ........................................ 514/44 A; 536/24.5

(58) Field of Classification Search
USPC ................... 514/44, 81; 536/24.5; 435/5, 6, 435/7.1, 91.2, 320.1; 530/327
See application file for complete search history.

(56) References Cited

U.S. PATENT DOCUMENTS

| | | | |
|---|---|---|---|
| 5,034,506 A | 7/1991 | Summerton et al. ........... 528/391 |
| 5,142,047 A | 8/1992 | Summerton et al. | |
| 5,166,315 A | 11/1992 | Summerton et al. ........... 528/406 |
| 5,185,444 A | 2/1993 | Summerton et al. | |
| 5,194,428 A | 3/1993 | Agrawal et al. ................... 514/44 |
| 5,217,866 A | 6/1993 | Summerton et al. ................ 435/6 |
| 5,495,006 A | 2/1996 | Climie et al. ................. 536/24.1 |
| 5,506,337 A | 4/1996 | Summerton et al. ........... 528/391 |
| 5,521,063 A | 5/1996 | Summerton et al. ................ 435/6 |
| 5,576,302 A | 11/1996 | Cook et al. | |
| 5,580,767 A | 12/1996 | Cowsert et al. | |
| 5,698,685 A | 12/1997 | Summerton et al. ......... 536/24.3 |
| 5,702,891 A | 12/1997 | Kolberg et al. | |
| 5,734,039 A | 3/1998 | Calabretta et al. | |
| 5,738,985 A * | 4/1998 | Miles et al. ........................ 435/5 |
| 5,801,154 A | 9/1998 | Baracchini et al. ............... 514/44 |
| 5,892,023 A | 4/1999 | Pirotzky et al. ............... 536/24.5 |
| 5,955,318 A | 9/1999 | Simons et al. | |
| 5,985,662 A | 11/1999 | Anderson et al. ............... 435/375 |
| 5,989,904 A * | 11/1999 | Das et al. ...................... 435/320.1 |
| 6,060,456 A | 5/2000 | Arnold et al. | |
| 6,133,246 A | 10/2000 | McKay et al. | |
| 6,174,868 B1 | 1/2001 | Anderson et al. | |
| 6,214,555 B1 * | 4/2001 | Leushner et al. .................. 435/6 |
| 6,228,579 B1 | 5/2001 | Zyskind et al. | |
| 6,239,265 B1 | 5/2001 | Cook | |
| 6,245,747 B1 | 6/2001 | Porter et al. ...................... 514/44 |
| 6,258,570 B1 * | 7/2001 | Glustein et al. .............. 435/91.2 |
| 6,306,993 B1 | 10/2001 | Rothbard et al. | |
| 6,365,351 B1 | 4/2002 | Iversen | |
| 6,365,577 B1 | 4/2002 | Iversen .......................... 514/44 |
| 6,391,542 B1 | 5/2002 | Anderson et al. .................. 435/6 |
| 6,495,663 B1 | 12/2002 | Rothbard et al. | |
| 6,667,152 B2 | 12/2003 | Miles et al. ........................ 435/5 |
| 6,677,153 B2 | 1/2004 | Iversen | |
| 6,784,291 B2 | 8/2004 | Iversen et al. | |
| 6,828,105 B2 | 12/2004 | Stein et al. ......................... 435/6 |
| 6,841,542 B2 | 1/2005 | Bartelmez et al. | |
| 6,841,675 B1 | 1/2005 | Schmidt et al. ............... 544/336 |
| 6,881,825 B1 * | 4/2005 | Robbins et al. ............... 530/327 |
| 7,049,431 B2 | 5/2006 | Iversen | |
| 7,094,765 B1 | 8/2006 | Iversen et al. | |

(Continued)

FOREIGN PATENT DOCUMENTS

EP      1288296 A2 *  3/2003
WO      WO93/01286    1/1993

(Continued)

OTHER PUBLICATIONS

Peter M. Fischer, Cellular uptake mechanisms and potential therapeutic utility of peptidic cell delivery vectors: progress 2001-2006, Published online 2006 in Wiley InterScience, www.interscience.wiley.com, pp. 1-41.*
McCaffrey et al., A potent and specific morpholino antisense inhibitor of hepatitis C translation in mice, Aug. 2003, Hepatology, vol. 38, pp. 503-508.*
Le et al., A common structural core in the internal ribosome entry sites of picornavirus, hepatitis C virus, and pestivirus, 1996, Virus Genes, vol. 12, pp. 135-147.*
Dildine et al., Poliovirus translation initiation: Differential effects of directed and selected mutations in the 5' noncoding region of viral RNAs, 1991, Virology, vol. 182, pp. 742-752.*
Moulton et al., HIV tat peptide enhances cellular delivery of antisense morpholino oligomers, 2003, Antisense and Nucleic Acid Drug Development, vol. 13, pp. 31-43.*
Agrawal et al. *Proc Natl Acad Sci U S A.*, 87(4):1401-5 (1990).

(Continued)

*Primary Examiner* — Dana Shin
(74) *Attorney, Agent, or Firm* — Seed IP Law Group PLLC

(57) ABSTRACT

The invention provides antisense antiviral compounds and methods of their use and production in inhibition of growth of viruses of the Picornaviridae family and in the treatment of a viral infection. The compounds are particularly useful in the treatment of *Enterovirus* and/or *Rhinovirus* infection in a mammal. The antisense antiviral compounds are substantially uncharged, morpholino oligonucleotides have a sequence of 12-40 subunits, including at least 12 subunits having a targeting sequence that is complementary to a region associated with viral RNA sequences within a 32 nucleotide region of the viral 5' untranslated region identified by SEQ ID NO:7.

8 Claims, 6 Drawing Sheets

(56) References Cited

U.S. PATENT DOCUMENTS

| | | | |
|---|---|---|---|
| 7,115,374 B2 | 10/2006 | Linnen et al. | |
| 7,468,418 B2 | 12/2008 | Iversen et al. | 530/300 |
| 7,507,196 B2 | 3/2009 | Stein et al. | 514/44 |
| 7,524,829 B2 | 4/2009 | Stein et al. | 514/44 |
| 7,582,615 B2 | 9/2009 | Neuman et al. | 514/44 |
| 2001/0024783 A1 | 9/2001 | Iversen | 435/6 |
| 2003/0166588 A1 | 9/2003 | Iversen et al. | 514/44 |
| 2003/0171311 A1 | 9/2003 | Blatt et al. | 514/44 |
| 2003/0171335 A1* | 9/2003 | Stein et al. | 514/81 |
| 2003/0224353 A1 | 12/2003 | Stein et al. | 435/5 |
| 2004/0072239 A1* | 4/2004 | Renaud et al. | 435/7.1 |
| 2004/0259108 A1 | 12/2004 | Linnen et al. | |
| 2004/0265879 A1* | 12/2004 | Iversen et al. | 435/6 |
| 2005/0096291 A1 | 5/2005 | Iversen et al. | 514/44 |
| 2005/0171044 A1 | 8/2005 | Stein et al. | 514/44 |
| 2005/0176661 A1 | 8/2005 | Vaillant et al. | |
| 2006/0063150 A1 | 3/2006 | Iversen et al. | |
| 2006/0148747 A1 | 7/2006 | Stein et al. | 514/44 |
| 2006/0149046 A1 | 7/2006 | Arar | |
| 2006/0269911 A1 | 11/2006 | Iversen et al. | |
| 2007/0004661 A1 | 1/2007 | Stein et al. | 514/44 |
| 2007/0066556 A1 | 3/2007 | Stein et al. | |
| 2007/0129323 A1 | 6/2007 | Stein et al. | 514/44 |
| 2007/0265214 A1 | 11/2007 | Stein et al. | 514/44 |
| 2008/0311556 A1 | 12/2008 | Iversen | 435/6 |
| 2009/0012280 A1 | 1/2009 | Stein et al. | 536/23.1 |
| 2009/0082547 A1 | 3/2009 | Iversen et al. | 530/322 |
| 2009/0088562 A1 | 4/2009 | Weller et al. | 536/24.5 |
| 2009/0099066 A1 | 4/2009 | Moulton et al. | 514/7 |
| 2009/0186847 A1 | 7/2009 | Stein et al. | 514/44 |
| 2009/0186848 A1 | 7/2009 | Stein et al. | 514/44 |
| 2009/0186849 A1 | 7/2009 | Stein et al. | 514/44 |
| 2010/0063133 A1 | 3/2010 | Neuman et al. | 514/44 A |

FOREIGN PATENT DOCUMENTS

| | | |
|---|---|---|
| WO | WO98/12312 | 3/1998 |
| WO | WO02/26968 | 4/2002 |
| WO | WO02/068637 A2 | 9/2002 |
| WO | WO03/033657 | 4/2003 |
| WO | WO03/033667 A2 | 4/2003 |
| WO | WO2005/007805 | 1/2005 |
| WO | WO2005/013905 | 2/2005 |
| WO | WO2005/030800 | 4/2005 |
| WO | WO2005/065268 | 7/2005 |
| WO | WO2006/033933 | 3/2006 |
| WO | WO2006/047683 | 5/2006 |
| WO | WO2006/050414 | 5/2006 |
| WO | WO2007/030576 | 3/2007 |
| WO | WO2007/030691 | 3/2007 |
| WO | WO2007/103529 | 9/2007 |

OTHER PUBLICATIONS

Bailey et al., "Cationic oligonucleotides can mediate specific inhibition of gene expression in *Xenopus* oocytes." *Nucleic Acids Res*, 26(21):4860-7 (1998).
Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).
Blommers et al., *Nucleic Acids Res.*, 22(20):4187-94 (1994).
Bonham et al., *Nucleic Acids Res.*, 23(7):1197-203 (1995).
Boudvillain et al., *Biochemistry* 36(10):2925-31 (1997).
Branch, Andrea D., *TIBS*, 23:45-50 (1998).
Brasey et al., *J. Virol.*, 77(7):3939-3949 (2003).
Cross et al., "Solution structure of an RNA × DNA hybrid duplex containing a 3'-thioformacetal linker and an RNA A-tract." *Biochemistry*, 36(14): 4096-107 (1997).
Dagle et al., "Targeted elimination of zygotic messages in *Xenopus laevis* embryos by modified oligonucleotides possessing terminal cationic linkages", *Nucleic Acids Res.*, 28(10): 2153-7 (2000).
Ding, D., et al., *Nucleic Acids Res* 24(2):354-60, (1996).
Egholm et al., "PNA hybridizes to complementary oligonucleotides obeying the Watson-Crick hydrogen-bonding rules." *Nature*, 365(6446): 566-8 (1993).

Felgner et al., *PNAS*, 84(21): 7413-7 (1987).
Gait et al., *J. Chem. Soc.*, 0(14)1684-1686 (1974).
Gee et al., *Antisense Nucleic Acid Drug Dev* 8(2):103-11 (1998).
Johannes et al., *PNAS*, 96(23):13118-23 (1999).
Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).
Linkletter, B. A. and Bruice, T.C., "Solid-phase synthesis of positively charged deoxynucleic guanidine (DNG) modified oligoriucleotidos containing neutral urea linkages: Effect of charge deletions on binding and fidelity." *Bioorg. Med. Chem.* 8(11): 1893-1901 (2000).
Micklefield, J., "Backbone modification of nucleic acids: synthesis, structure and therapeutic applications." *Curr Med Chem*, 8(10):1157-79 (2001).
Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.
Moulton, H. M., M. H. Nelson, et al., *Bioconjug Chem* 15(2): 290-9 (2004).
Nelson et al., "Arginine-rich peptide conjugation to morpholino oligomers: effects on antisense activity and specificity." *Bioconjug Chem.*, 16(4): 959-66 (2005).
Stein, D., et al., *Antisense Nucleic Acid Drug Dev* 7(3):151-7, (1997).
Summerton et al., *Antisense & Nucleic Acid Drug Development*, 7:63-70 (1997).
Summerton et al., *Biochim et. Biophys. ACTA*, 1489:141-158 (1999).
Summerton, J. and D. Weller, "Morpholino antisense oligomers: design, preparation, and properties.", *Antisense Nucleic Acid Drug Dev.*, 7(3): 187-95 (1997).
Toulme et al., Targeting RNA structures by antisense oligonucleotides. *Biochimie*, 78(7): 663-73 (1996).
Wilson et al., *Mol. Cell Biol.*, 20(14):4990-4999 (2000).
U.S. Appl. No. 11/431,968, filed May 10, 2006, Stein et al.
Banerjee, R. and A. Dasgupta (2001). "Interaction of picornavirus 2C polypeptide with the viral negative-strand RNA." *J Gen Virol* 82(Pt 11):2621-7.
Banerjee, R. and A. Dasgupta (2001). "Specific interaction of hepatitis C virus protease/helicase NS3 with the 3'-terminal sequences of viral positive- and negative-strand RNA." *J Virol* 75(4):1708-21.
Banerjee, R., A. Echeverri, et al. (1997). "Poliovirus-encoded 2C polypeptide specifically binds to the 3'-terminal sequences of viral negative-strand RNA." J Virol 71(12):9570-8.
Banerjee, R., W. Tsai, et al. (2001). "Interaction of poliovirus-encoded 2C/2BC polypeptides with the 3' terminus negative-strand cloverleaf requires an intact stem-loop b." *Virology*, 280(1):41-51.
Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19):11047-52. (1998).
Clarke et al., *J. Infect. Diseases*, 181:S309-S316 (2000).
Corey et al., Morpgolino Antisnese Oligonucleotides: Tools for Investigating Vertebrate Development, Genome Biology, 2(5):1015.1-1015.3 (2001).
Freier, S.M., In Antisense Drug Technology: Principles, Strategies, and Applications, Ch. 5, pp. 107-118, (2001).
Genbank Accession No. AF304460.
Green et al., *J. Am. Coll. Surg.*, 191:93-105 (2000).
Hanecak et al., *Journal of Virology*, 70(8):5203-5212 (1996).
Holland et al., Emerging Virus, Morse, S.S., Ed., Oxford University Press, New York and Oxford pp. 203-218 (1993).
Jaeger, J.A., et al., Proc. Natl. Acad. Sci. USA 86:7706-7710, (1989).
Lopez De Quinto S. et al., *Virology*, 255(2):324-336 (1999).
Markoff, L., *Adv. Virus Res.*, 59:177-228 (2003).
Moulton et al., Abstracts of Papers American Chemical Society National Meeting 226 (1-2): Biol 75 (Sep. 7-11, 2003).
National Center for Biotechnology Information Report No. AF029248 from NCBI Genome Database (2000).

National Center for Biotechnology Information Report No. NC_002645 from NCBI Genome Database (2001).
National Center for Biotechnology Information Report No. AY274119 from NCBI Genome Database (2003).
Neuman, B.W., et al., *Journal of Virology* 78(11):5891-5899, (2004).
O'Ryan et al., In: Spector S, Lancz G, Eds., Clinical Virology Manual, New York, Elsevier Science pp. 361-396 (1992).
Orr et al., *Current Opinion in Molecular. Therapeuctics*, Current Drugs, 2(3):325-331 (2000).
Pardigon, N. and J. H. Strauss (1992). "Cellular proteins bind to the 3' end of Sindbis virus minus-strand RNA." *J Virol.*, 66(2):1007-15.
Pardigon, N., E. Lenches, et al. (1993). "Multiple binding sites for cellular proteins in the 3' end of Sindbis alphavirus minus-sense RNA." *J Virol.*, 67(8):5003-11.
Partridge et al., Antisense Nucleic Acid Drug Development, 6(3):169-175 (1996).
Paul, A. V. (2002). Possible unifying mechanism of picornavirus genome replication. *Molecular Biology of Picornaviruses.* B. L. Semler and E. Wimmer. Washington, DC, ASM Press:227-246.
Roehl, H. H. and B. L. Semler (1995). "Poliovirus infection enhances the formation of two ribonucleoprotein complexes at the 3' end of viral negative-strand RNA." *J Virol.*, 69(5):2954-61.
Roehl, H. H., T. B. Parsley, et al. (1997). "Processing of a cellular polypeptide by 3CD proteinase is required for poliovirus ribonucleoprotein complex formation." *J Virol.* 71(1):578-85.
Rothbard et al., *J. Med. Chem.*, 45:3612-3618 (2002).
Sankar e al., *European Journal of Biochemistry*, 184(1):39-45 (1989).
Siprashvili, Z., et al., Human Gene Therapy 14:1225-1233 (2003).
Smith et al., *Emerg. Inf. Dis.*, 4:13-20 (1998).
Smith, R.M. and Wu, G.Y., Journal of Viral Hepatitis 11:115-123 (2004).
Stein et al., *Antisense Nucleic Acid Drug Development*, 11(5):317-325 (2001).
Thiel et al., *Journal of General Virology*, 82:1273-1281 (2001).
Wages et al., *Biotechniques*, 23:1116-1121 (1997).
Wang et al., *Antimicrobial Agents Chemotherapy*, 45(4):1043-1052 (2001).
Wei et al., *Nucleic Acids Res.*, 28:3065-3074 (2000).
Wu et al., *J. Biol. Chem.*, 267:12436-12439 (1992).
Xu et al., *Revue Scientifique Technique*, Office of International des Epizooties 10:2393-2408 (1991).
Xu, W. Y. (1991). "Viral haemorrhagic disease of rabbits in the People's Republic of China: epidemiology and virus characterisation." *Rev Sci Tech*, 10(2): 393-408.
Zhang et al., *Antimicrobial Agents Chemotherapy*, 43(2):347-353 (1999).
Zuker, M., *Nucleic Acids Res.*, 31(13):3406-3415 (2003).
Agrawal et al., "Antisense therapeutics: is it as simple as complementary base recognition?" Molecular Medicine Today 6: 72-81, 2000.
Agrawal et al., "Oligodeoxynucleoside phosphoramidates and phosphorothioates as inhibitors of human immunodeficiency virus" Proc. Natl. Acad. Sci. USA 85(19): 7079-7083, 1988.
Anderson et al , "Inhibition of Human Cytomegalovirus Immediate-Early Gene Expression by an Antisense Oligonucleotide Complementary to Immediate-Early RNA" Antimicrobial Agents and Chemotherapy 40(9): 2004-2011, 1996.
Burnett et al., "The Evolving Field of Biodefence: Therapeutic Developments and Diagnostics" Nature Reviews 4: 281-297, 2005.
Callahan et al., "Molecular cloning and complete sequence determination of RNA genome of human rhinovirus type 14" Proc. Natl. Acad. Sci. USA 82: 732-736, 1985.
Corver et al., "Fine Mapping of a *cis*-Acting Sequence Element in Yellow Fever Virus RNA That Is Required for RNA Replication and Cyclization" Journal of Virology 77(3): 2265-2270, 2003.
Crooke et al., "In Vitro Toxicological Evaluation of ISIS 1082, a Phosphorothiate Oligonucleotide Inhibitor of Herpes Simplex Virus" Antimicrobial Agents and Chemotherapy 36(3): 527-532, 1992.
Deas et al , "Inhibition of Flavivirus Infections by Antisense Oligomers Specifically Suppressing Viral Translation and RNA Replication" Journal of Virology 79(8): 4599-4609, 2005.

Faria et al., "Phosphoramidate oligonucleotides as potent antisense molecules in cells and in vivo" Nature Biotechnology 19(1): 40-44, 2001.
Feldmann et al., "Ebola virus: from discovery to vaccine" Nature Reviews 3(8): 677-685, 2003.
Geisbert et al., "Ebola virus: new insights into disease aetiopathology and possible therapeutic interventions" Expert Reviews in Molecular Medicine 6(20): 1-24, 2004.
GenBank Accession No. V01149, "Human poliovirus 1 Mahoney, complete genome" retrieved from http://www.ncbi.nlm.nih.gov/nuccore/61252, May 12, 2010.
Hahn et al., "Conserved Elements in the 3' Untranslated Region of Flavivirus RNAs and Potential Cyclization Sequences" Journal of Molecular Biology 198(1): 33-41, 1987.
Hudziak et al., "Resistance of Morpholino Phosphorodiamidate Oligomers to Enzymatic Degradation" Antisense & Nucleic Acid Drug Development 6: 267-272, 1996.
International Search Report (US), mailed Nov. 25, 2003, for PCT/US02/32868, 6 pages.
International Search Report (US), mailed Mar. 27, 2006, for PCT/US04/12623, 3 pages.
International Search Report (US), mailed Nov. 18, 2005, for PCT/US04/43341, 4 pages.
International Search Report (US), mailed Jul. 12, 2006, for PCT/US05/38780, 5 pages.
International Search Report (US), mailed Aug. 29, 2007, for PCT/US05/39607, 4 pages.
International Search Report (US), mailed Oct. 23, 2007, for PCT/US07/05977, 2 pages.
Iversen, P., "Antisense Antiviral Compound and Method for Treating Influenza Viral Infection" U.S. Appl. No. 61/261,278, filed Nov. 13, 2009.
Iversen, P., "Antisense Antiviral Compound and Method for Treating Influenza Viral Infection" U.S. Appl. No. 61/292,056, filed Jan. 4, 2010.
Jen et al., "Suppression of Gene Expression by Targeted Disruption of Messenger RNA: Available Options and Current Strategies" Stem Cells 18: 307-319, 2000.
Jubin et al., "Hepetitis C Virus Internal Ribosome Entry Site (IRES) Stem Loop IIId Contains a Phylogenetically Conserved GGG Triplet Essential for Translation and IRES Folding" Journal of Virology 74(22): 10430-10437, 2000.
Khromykh et al., "Essential Role of Cyclization Sequences in Flavivirus RNA Replication" Journal of Virology 75(14): 6719-6728, 2001.
Kinney et al , "Inhibition of Dengue Virus Serotypes 1 to 4 in Vero Cell Cultures with Morpholino Oligomers" Journal of Virology 79(8): 5116-5128, 2005.
Lee et al., "Complete Sequence of the RNA Genome of Human Rhinovirus 16, a Clinically Useful Common Cold Virus Belonging to the ICAM-1 Receptor Group" Virus Genes 9(2): 177-181, 1994.
Liu et al., "Structural and Functional Analysis of the 5' Untranslated Region of Coxsackievirus B3 RNA: In Vivo Translational and Infectivity Studies of Full-Length Mutants" Virology 265: 206-217, 1999.
Mizuta et al., "Antisense oligonucleotides directed against the viral RNA polymerase gene enhance survival of mice infected with influenza A" Nature Biotechnology 17(6): 583-587, 1999.
NCBI Genbank Nucleotide Accession No. AF091736, VESV-like calicivirus strain Pan-1, complete genome, retrieved from http://www.ncbi.nlm.nih.gov/nuccore/3661574, May 19, 2009.
Pari et al., "Potent Antiviral Activity of an Antisense Oligonucleotide Complementary to the Intron-Exon Boundary of Human Cytomegalovirus Genes UL36 and UL37" Antimicrobial Agent and Chemotherapy 39(5): 1157-1161, 1995.
Raviprakash et al , "Inhibition of Dengue Virus by Novel, Modified Antisense Oligonucleotides" Journal of Virology 69(1): 67-74, 1995.
Robaczewska et al., "Inhibition of hepadnaviral replication by polyethylenimine-based intravenous delivery of antisense phosphodiester oligodeoxynucleotides to the liver" Gene Therapy 8: 874-881, 2001.
Scanlon, "Anti-Genes: siRNA, Ribozymes and Antisense" Current Pharmaceutical Biotechnology 5(5): 415-420, 2004.

Shengqi et al., "Synthesis of Antisense Phosphothioate Oligodeoxynucleotides of Dengue Fever Virus and Their Anti-Viral Activity" Progress of Biochemistry and Biophysics 24(1): 64-68, 1997 (English Translation).

Smith et al., "Antisense treatment of *Caliciviridae*: An emerging disease agent of animals and humans" Current Opinion in Molecular Therapeutics 4(2): 177-184, 2002.

Stone et al., "A Morpholino Oligomer Targeting Highly Conserved Internal Ribosome Entry Site Sequence Is Able to Inhibit Multiple Species of Picornavirus" Antimicrobial Agents and Chemotherapy 52(6): 1970-1981, 2008.

Taylor et al., "Antisense oligonucleotides: a systematic high-throughput approach to target validation and gene function determination" Drug Discovery Today 4(12): 562-567, 1999.

Vlasov et al., "Inhibition of the Influenza Virus M Protein mRNA Translation in vitro with Complementary Oligonucleotides" Nucleosides & Nucleotides 10(1-3): 649-650, 1991.

Yuan et al., "A phosphorothioate antisense oligodeoxynucleotide specifically inhibits coxsackievirus B3 replication in cardiomyocytes and mouse hearts" Laboratory Investigation 84: 703-714, 2004.

Cantor et al., "Comparison of the Antiviral Efficacy of Ribozymes and Antisense RNA Directed Against Bovine Leukemia Virus *rex/tax*," Antisense Nucleic Acid Drugs Dev.6:301-304, 1996.

Geller et al., "Antisense Antibacterial Method and Compound," Office Action mailed Sep. 29, 2010, U.S. Appl. No. 11/173,847, 25 pages.

Iversen et al., "Oligonucleotide Analog and Method for Treating Flavivirus Infections," *Ex Parte* Patrick L. Iversen and David A. Stein mailed Apr. 1, 2010, for U.S. Appl. No. 10/913,996, 12 pages.

Iversen et al., "Splice-Region Antisense Composition and Method," Office Action mailed on Apr. 23, 2010, U.S. Appl. No. 11/433,214, 17 pages.

Iversen et al., "Antisense Antiviral Compound and Method for Treating ssRNA Viral Infection," Office Action mailed Oct. 19, 2010, U.S. Appl. No. 11/432,031, 25 pages.

Sioud et al., "Prevention of human immunodeficiency virus type 1 integrase expression in *Escherichia coli* by ribozyme," *Proc. Natl. Acad. Sci. USA* 88:7303-7307, 1991.

Stein et al., "Antisense Antiviral Agent and Method for Treating ssRNA Viral Infection," Office Action mailed Feb. 17, 2010, U.S. Appl. No. 11/431,968, 19 pages.

Vickers et al., "Effects of RNA secondary structure on cellular antisense activity," *Nucleic Acid Research* 28(6):1340-1347, 2000.

Watts et al., "Architecture and secondary structure of an entire HIV-1 RNA genome," *Nature* 460:711-716, 2009.

Office Action mailed Aug. 18, 2010, U.S. Appl. No. 11/801,885, 6 pages.

Advisory Action mailed Oct. 28, 2010, U.S. Appl. No. 11/801,885, 6 pages.

Zhang et al., "Inhibition of Viral Replication by Ribozyme: Mutational Analysis of the Site and Mechanism of Antiviral Activity," *Journal of Virology* 79(6):3728-3736, 2005.

\* cited by examiner

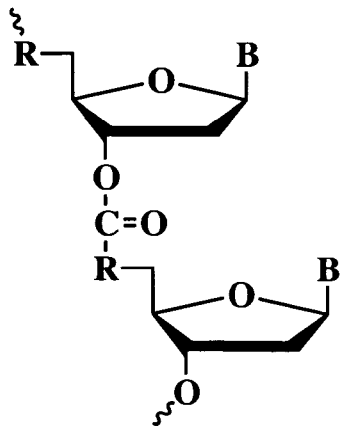
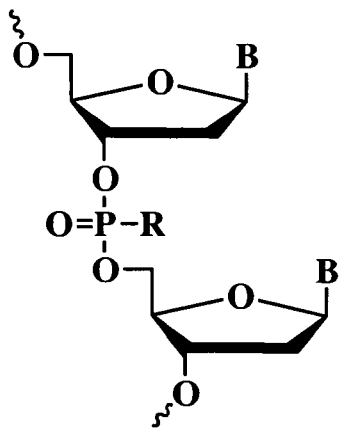
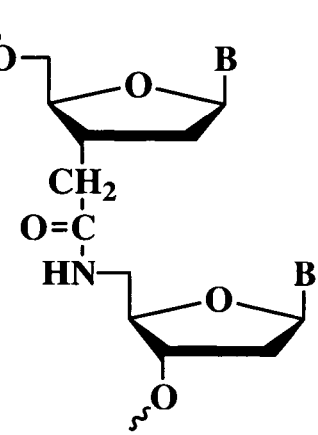
Fig. 2A          Fig. 2B          Fig. 2C
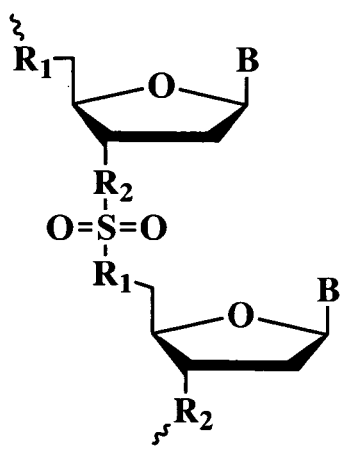
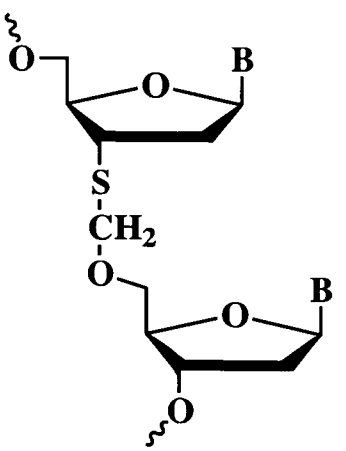
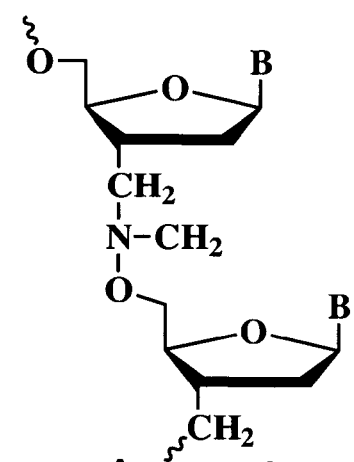
Fig. 2D          Fig. 2E          Fig. 2F
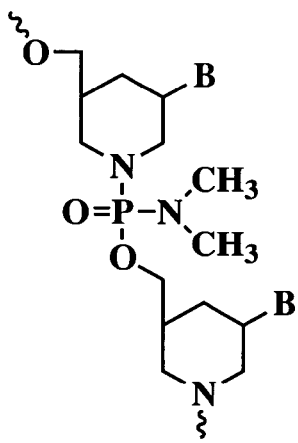
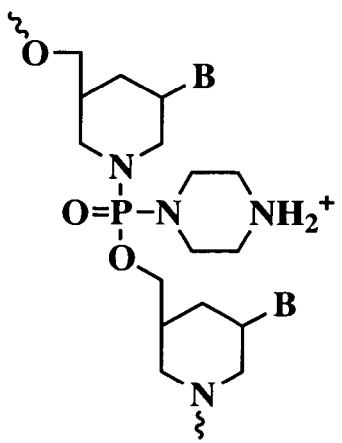
Fig. 2G          Fig. 2H

```
              * * * * * * * * * * * * * * * * *   * *   * * *   *     * * *
          5   TCCTCCGGCCCCTGAATGTGGCTAACCTTAAC
          6   TCCTCCGGCCCCTGAATGCGGCTAACCTTAAC
          3   TCCTCCGGCCCCTGAATGCGGCTAATCCTAAC
SEQ ID NOS: 4 TCCTCCGGCCCCTGAATGCGGTTAATCCTAAC
          2   TCCTCCGGCCCCTGAATGCGGTTAATCCTAAC
          1   TCCTCCGGCCCCTGAATGCGGCTAATCCCAAC
          7   TCCTCCGGCCCCTGAATGYGGCTAAYCYYAAC
```

⟵――――― 5'-32 Target Region ―――――⟶

Fig. 3

SEQUENCE LISTING

<160> NUMBER OF SEQ ID NOS: 21

<210> SEQ ID NO 1
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 1
tcctccggcc cctgaatgcg gctaatccca ac                                    32

<210> SEQ ID NO 2
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 2
tcctccggcc cctgaatgcg gctaatccta ac                                    32

<210> SEQ ID NO 3
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 3
tcctccggcc cctgaatgcg gctaatccta ac                                    32

<210> SEQ ID NO 4
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 4
tcctccggcc cctgaatgcg gttaatccta ac                                    32

<210> SEQ ID NO 5
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 5
tcctccggcc cctgaatgtg gctaacctta ac                                    32

<210> SEQ ID NO 6
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 6
tcctccggcc cctgaatgcg gctaacctta ac                32

<210> SEQ ID NO 7
<211> LENGTH: 32
<212> TYPE: DNA
<213> ORGANISM: Artificial Sequence
<220> FEATURE:
<223> OTHER INFORMATION: Synthetic Target Sequence based on Picornavirus
      Sequence

<400> SEQUENCE: 7
tcctccggcc cctgaatgyg gctaaycyya ac                32

<210> SEQ ID NO 8
<211> LENGTH: 32
<212> TYPE: DNA
<213> ORGANISM: Artificial Sequence
<220> FEATURE:
<223> OTHER INFORMATION: Synthetic Oligomer

<400> SEQUENCE: 8
gttgggatta gccgcattca ggggccggag ga                32

<210> SEQ ID NO 9
<211> LENGTH: 32
<212> TYPE: DNA
<213> ORGANISM: Artificial Sequence
<220> FEATURE:
<223> OTHER INFORMATION: Synthetic Oligomer

<400> SEQUENCE: 9
gttggggttg gccgcattca ggggccggag ga                32

<210> SEQ ID NO 10
<211> LENGTH: 32
<212> TYPE: DNA
<213> ORGANISM: Artificial Sequence
<220> FEATURE:
<223> OTHER INFORMATION: Synthetic Oligomer

<400> SEQUENCE: 10
gttgggrttr gccgcattca ggggccggag ga                32

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 11
ccgcattcag gggccggagg                              20

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 12
ggattagccg cattcagggg cc                           22

<210> SEQ ID NO 13
<211> LENGTH: 21
<212> TYPE: DNA
<213> ORGANISM: Artificial Sequence -continued

```
<220> FEATURE:
<223> OTHER INFORMATION: Synthetic Oligomer

<400> SEQUENCE: 13
gttgggatta gccgcattca g                                              21

<210> SEQ ID NO 14
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (12)...(12)
<223> OTHER INFORMATION: Xaa is 6-aminohexanoic acid
<220> FEATURE:
<221> NAME/KEY: MOD_RES
<222> LOCATION: (13)...(13)
<223> OTHER INFORMATION: Xaa is beta-alanine

<400> SEQUENCE: 14

Arg Arg Arg Arg Arg Arg Arg Arg Arg Phe Phe Xaa Xaa
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(13)
<223> OTHER INFORMATION: Xaa is 6-aminohexanoic acid
<220> FEATURE:
<221> NAME/KEY: MOD_RES
<222> LOCATION: (14)...(14)
<223> OTHER INFORMATION: Xaa is beta-alanine

<400> SEQUENCE: 15

Arg Xaa Arg Arg Xaa Arg Arg Xaa Arg Arg Xaa Arg Xaa Xaa
 1               5                  10

<210> SEQ ID NO 16
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(16)
<223> OTHER INFORMATION: Xaa is 6-aminohexanoic acid
<220> FEATURE:
<221> NAME/KEY: MOD_RES
<222> LOCATION: (17)...(17)
<223> OTHER INFORMATION: Xaa is beta-alanine

<400> SEQUENCE: 16

Arg Xaa Arg Xaa Arg Xaa Arg Xaa Arg Xaa Arg Xaa Arg Xaa Arg Xaa
 1               5                  10                  15
Xaa

<210> SEQ ID NO 17
<211> LENGTH: 9
<212> TYPE: PRT
<213> ORGANISM: Artificial Sequence
<220> FEATURE:
<223> OTHER INFORMATION: Synthetic arginine-rich peptide
<220> FEATURE:
```

```
<221> NAME/KEY: MOD_RES
<222> LOCATION: (2)...(8)
<223> OTHER INFORMATION: Xaa is 6-aminohexanoic acid
<220> FEATURE:
<221> NAME/KEY: MOD_RES
<222> LOCATION: (9)...(9)
<223> OTHER INFORMATION: Xaa is beta-alanine

<400> SEQUENCE: 17

Arg Xaa Arg Xaa Arg Xaa Arg Xaa Xaa
 1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(7)
<223> OTHER INFORMATION: Xaa is 6-aminohexanoic acid
<220> FEATURE:
<221> NAME/KEY: MOD_RES
<222> LOCATION: (8)...(8)
<223> OTHER INFORMATION: Xaa is beta-alanine

<400> SEQUENCE: 18

Arg Xaa Arg Arg Xaa Arg Xaa Xaa
 1               5

<210> SEQ ID NO 19
<211> LENGTH: 11
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)...(10)
<223> OTHER INFORMATION: Xaa is 6-aminohexanoic acid
<220> FEATURE:
<221> NAME/KEY: MOD_RES
<222> LOCATION: (11)...(11)
<223> OTHER INFORMATION: Xaa is beta-alanine

<400> SEQUENCE: 19

Arg Xaa Arg Arg Xaa Arg Arg Xaa Arg Xaa Xaa
 1               5                  10

<210> SEQ ID NO 20
<211> LENGTH: 21
<212> TYPE: DNA
<213> ORGANISM: Artificial Sequence
<220> FEATURE:
<223> OTHER INFORMATION: SyntheticTarget Sequence based on Picornavirus
      Sequence

<400> SEQUENCE: 20
ccggggaaac agaagtgctt g                                               21

<210> SEQ ID NO 21
<211> LENGTH: 20
<212> TYPE: DNA
<213> ORGANISM: Artificial Sequence
<220> FEATURE:
<223> OTHER INFORMATION: SyntheticTarget Sequence based on Picornavirus
      Sequence
```

```
<400> SEQUENCE: 21
ggaaacacgg acacccaaag                                              20
```

METHOD FOR TREATING ENTEROVIRUS OR RHINOVIRUS INFECTION USING ANTISENSE ANTIVIRAL COMPOUNDS

CROSS-REFERENCE TO RELATED APPLICATIONS

This application claims the benefit of U.S. Provisional Application No. 60/716,001, filed Sep. 8, 2005 and U.S. Provisional Application No. 60/800,145, filed May 11, 2006, both incorporated herein by reference in their entirety.

FIELD OF THE INVENTION

This invention relates to antisense oligonucleotide compounds for use in treating a picornavirus infection and antiviral treatment methods employing the compounds.

REFERENCES

Agrawal, S., S. H. Mayrand, et al. (1990). *Proc Natl Acad Sci USA* 87(4): 1401-5.
Blommers, M. J., U. Pieles, et al. (1994). *Nucleic Acids Res* 22(20): 4187-94.
Bonham, M. A., S. Brown, et al. (1995). *Nucleic Acids Res* 23(7): 1197-203.
Boudvillain, M., M. Guerin, et al. (1997). *Biochemistry* 36(10): 2925-31.
Brasey, A., M. Lopez-Lastra, et al. (2003). *J Virol* 77(7): 3939-49.
Cross, C. W., J. S. Rice, et al. (1997). *Biochemistry* 36(14): 4096-107.
Dagle, J. M., J. L. Littig, et al. (2000). *Nucleic Acids Res* 28(10): 2153-7.
Ding, D., S. M. Grayaznov, et al. (1996). *Nucleic Acids Res* 24(2): 354-60.
Egholm, M., O. Buchardt, et al. (1993). *Nature* 365(6446): 566-8.
Felgner, P. L., T. R. Gadek, et al. (1987). *Proc Natl Acad Sci USA* 84(21): 7413-7.
Gait, M. J., A. S. Jones, et al. (1974). *J Chem Soc [Perkin 1]* 0(14): 1684-6.
Gee, J. E., I. Robbins, et al. (1998). *Antisense Nucleic Acid Drug Dev* 8(2): 103-11.
Johannes, G., M. S. Carter, et al. (1999). *Proc Natl Acad Sci USA* 96(23): 13118-23.
Lesnikowski, Z. J., M. Jaworska, et al. (1990). *Nucleic Acids Res* 18(8): 2109-15.
Mertes, M. P. and E. A. Coats (1969). *J Med Chem* 12(1): 154-7.
Moulton, H. M., M. H. Nelson, et al. (2004). *Bioconjug Chem* 15(2): 290-9.
Nelson, M. H., D. A. Stein, et al. (2005). *Bioconjug Chem* 16(4): 959-66.
Strauss, J. H. and E. G. Strauss (2002). *Viruses and Human Disease*. San Diego, Academic Press.
Summerton, J. and D. Weller (1997). *Antisense Nucleic Acid Drug Dev* 7(3): 187-95.
Toulme, J. J., R. L. Tinevez, et al. (1996). *Biochimie* 78(7): 663-73.
Wilson, J. E., M. J. Powell, et al. (2000). *Mol Cell Biol* 20(14): 4990-9.

BACKGROUND OF THE INVENTION

The Picornaviridae represents a very large family of small RNA viruses responsible for many serious human and animal diseases (Straus and Straus, 2002). The Picornaviridae includes four major genera: *Enterovirus, Rhinovirus, Apthovirus* and *Hepatovirus*. The *Enterovirus* genus includes polioviruses, coxsackieviruses, echoviruses, and enteroviruses.

Poliovirus is the etiologic agent of the disease poliomyelitis in humans, and there are three known serotypes of the virus. The oral poliovaccine, typically given to children, is a mixture of the Sabin strain of the virus. The oral poliovirus vaccine is safe and effective, yet has two limitations. First, the vaccine is unstable since current vaccines are inactivated by relatively brief (less than 24 hours) exposure to temperatures of 37° C. This necessitates transport in a frozen state to the locale where they are administered. Second, the vaccine occasionally reverts to virulence in vaccine recipients and the reverted virulent virus may then be passed to other individuals who come into contact with the recipient in whom the vaccine has reverted.

The human rhinoviruses consist of at least 100 serotypes and are the primary causative agents of the common cold. Because of the large number of serotypes, development of a vaccine is problematic and antiviral agents may therefore be the best approach to treatment. The Coxsackie viruses and other human enteroviruses (multiple serotypes), are associated with a wide range of human diseases including summer flus, diarrhea, meningitis, hepatitis, pneumonia, myocarditis, pericarditis, and diabetes. These infections occur sporadically in the general population, but are becoming more common among children in day care and their parents and siblings. Other important members of the Picornaviridae family include human hepatitis A virus, Theiler's murine encephalomyelitis virus, foot-and-mouth disease virus, and mengovirus.

The existing drugs which are used against the viruses described above are only moderately effective, and are typically effective against only a limited subset of the rhinovirus serotypes. In general, the available drugs have either failed to demonstrate sufficient prophylactic effects or are converted in the body into inactive metabolites.

Thus, there remains a need for a more effective antiviral therapy in several members of the Picornoviridae family.

SUMMARY OF THE INVENTION

The invention includes, in one aspect, a method of inhibiting viral infection in mammalian cells by an *Enterovirus* or *Rhinovirus* in the Picornaviridae family. The method includes the steps of exposing the cells to an antisense oligonucleotide compound, thereby to form a heteroduplex structure (i) composed of the virus' positive sense strand and the oligonucleotide compound, and (ii) characterized by a Tm of dissociation of at least 45° C. The oligonucleotide compound is characterized by:

(i) a substantially uncharged, nuclease-resistant backbone,
(ii) capable of uptake by mammalian host cells,
(iii) containing between 12-40 nucleotide bases, and
(iv) having a targeting sequence of at least 12 subunits complementary to SEQ ID NO:7 in the positive-sense strand of the virus.

The compound to which the host cells are exposed may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

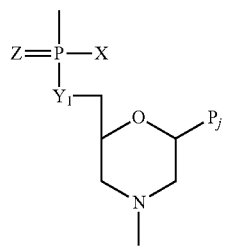

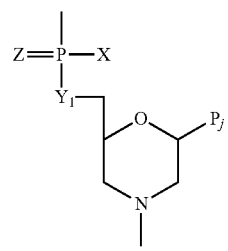

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino, e.g., wherein X=$NR_2$, where each R is independently hydrogen or methyl.

The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The oligonucleotide compound to which the cells are exposed may have a sequence contained in SEQ ID NO:10, such as one of the sequences identified by SEQ ID NO:11, SEQ ID NO:12 or SEQ ID NO:13. The compound may be conjugated to an arginine-rich polypeptide effective to promote uptake of the compound into infected host cells. Exemplary polypeptides have one of the sequences identified as SEQ ID NOS:14-19.

For use in treating a mammalian subject infected by an *Enterovirus* or *Rhinovirus* in the Picornaviridae family, the compound is administered to the subject in a pharmaceutically effective amount. Compound administration may be continued until a significant reduction in viral infection or the symptoms thereof is observed. The subject may be treated with a second anti-viral compound before, after, or during treatment with the oligonucleotide compound.

For use in treating a mammalian subject at risk of infection by an *Enterovirus* or *Rhinovirus* in the Picornaviridae family, the compound is administered to the subject in an amount effective to inhibit infection of subject host cells by the virus.

In another aspect, the invention includes an oligonucleotide compound for use in inhibiting viral infection in mammalian cells by an *Enterovirus* or *Rhinovirus* in the Picornaviridae family. The compound is characterized by:

(i) a substantially uncharged, nuclease-resistant backbone, (ii) capable of uptake by mammalian host cells, (iii) containing between 12-40 nucleotide bases, (iv) having a targeting sequence of at least 12 subunits contained in SEQ ID NO:10; and (v) capable of binding to the virus' positive sense strand to form a heteroduplex structure having by a Tm of dissociation of at least 45° C.

The compound may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino, e.g., wherein X=$NR_2$, where each R is independently hydrogen or methyl.

The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The oligonucleotide compound may have one of the sequences identified by SEQ ID NOS:11, 12, and 13. The compound may be conjugated to an arginine-rich polypeptide effective to promote uptake of the compound into infected host cells. Exemplary polypeptides have one of the sequences identified as SEQ ID NOS:14-19.

The compound may be formulated in combination with another anti-viral compound.

These and other objects and features of the invention will become more fully apparent when the following detailed description of the invention is read in conjunction with the accompanying drawings.

BRIEF DESCRIPTION OF THE FIGURES

FIGS. 2A-2G show examples of uncharged linkage types in oligonucleotide analogs. FIG. 2H is an example of a preferred charged, cationic linkage.

FIG. 3 shows the sequence conservation across a broad spectrum of picornaviruses for the 5'-32 nct region represented by SEQ ID NOS:1-6, and the combined sequence identified by SEQ ID NO:7.

DETAILED DESCRIPTION OF THE INVENTION

I. Definitions

The terms below, as used herein, have the following meanings, unless indicated otherwise:

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone. An oligonucleotide analog is also referred to herein as an oligonucleotide or oligonucleotide compound or oligonucleotide analog compound.

A substantially uncharged, phosphorus containing backbone in an oligonucleotide analog is one in which a majority of the subunit linkages, e.g., between 50-100%, typically at least 80% of its linkages, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 1A-1D where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference in their entirety.

Figure 1A:
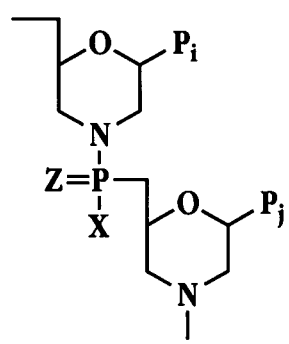
FIGS. 1A-1D show the repeating subunit segment of exemplary morpholino oligonucleotides, designated A through D.
Figure 1B:
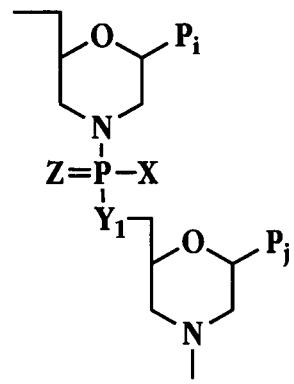

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 2B, where X=$NH_2$, NHR, or $NR_2$ (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2G. Also preferred are morpholino oligomers where the phosphordiamidate linkages are uncharged linkages as shown in FIG. 2G interspersed with cationic linkages as shown in FIG. 2H where, in FIG. 2B, X=1-piperazino. In another FIG. 2B embodiment, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "picornavirus" refers to one or more viral species belonging to the Picornaviridae family and specifically the *Enterovirus* and *Rhinovirus* genera of the Picornaviridae.

As used herein, the term "target" refers to a viral genomic RNA, and specifically, to a region identified by SEQ ID NO:7 within the 5'-untranslated region (5'-UTR) of the positive-sense RNA strand of a member of the Picornaviridae described herein.

The term "target sequence" refers to a portion of the target RNA against which the oligonucleotide analog is directed, that is, the sequence to which the oligonucleotide analog will hybridize by Watson-Crick base pairing of a complementary sequence.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases from the analog, but may alternatively be formed of non-contiguous sequences that when placed together, e.g., from opposite ends of the analog, constitute a sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting picornavirus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, polyarginine, or combinations of arginine and other amino acids including the non-natural amino acids 6-aminohexanoic acid and beta-alanine. Exemplary arginine-rich delivery peptides are listed as SEQ ID NOS:14-19. These exemplary arginine-rich delivery peptides facilitate transport into the target host cell as described (Moulton, Nelson et al. 2004; Nelson, Stein et al. 2005).

Rules for the selection of targeting sequences capable of inhibiting replication of picornaviruses are discussed below.

II. Targeted Viruses

The present invention is based on the discovery that effective inhibition of members of the Picornaviridae family can be achieved with antisense oligonucleotide analog compounds that (i) target the region identified by SEQ ID NO:7 of the 5' untranslated region (UTR) of the virus' positive strand, and (ii) have physical and pharmacokinetic features which allow effective interaction between the antisense compound and the virus within host cells. In one aspect, the oligomers can be used in treating a mammalian subject infected with the virus.

The invention targets single stranded, positive sense RNA viruses that are members of the Picornaviridae family. In particular, targeted viruses include members of the *Enterovirus* and *Rhinovirus* genera of the Picornaviridae family. Table 1 lists the viruses targeted by the invention as organized by genus. Various physical, morphological, and biological characteristics of members of the Picornaviridae family can be found, for example, in Textbook of Human Virology, R. Belshe, ed., $2^{nd}$ Edition, Mosby, 1991, at the Universal Virus Database of the International Committee on Taxonomy of Viruses and in human virology textbooks (e.g., see Strauss and Strauss, 2002). Some of the key biological characteristics of the Picornaviridae family of viruses are described below.

TABLE 1

Targeted Viruses of the Invention

| Family | Genus | Virus |
|---|---|---|
| Picornaviridae | *Enterovirus* | Poliovirus (PV) |
| | | Human enterovirus A (HEV-A) |
| | | Human enterovirus B (HEV-B) |
| | | Human enterovirus C (HEV-C) |
| | | Human enterovirus D (HEV-D) |
| | *Rhinovirus* | Human Rhinovirus A (HRV-89) |
| | | Human Rhinovirus B (HRV-14) |

Picornaviruses

GenBank reference entries for exemplary viral nucleic acid sequences representing picornavirus genomic RNA are listed in Table 2 below. The nucleotide sequence numbers in Table 2 are derived from the Genbank reference for the positive-strand RNA. It will be appreciated that these sequence references are only illustrative of other sequences in the Picornaviridae family, as may be available from available gene-sequence databases or literature or patent resources.

Table 2 lists the targets for a 32-base sequence corresponding to nucleotides 443-474 of the poliovirus reference sequence (NC 002058) and contained in the 5' UTR region of several picornaviruses. All the viruses listed in Table 2 are human isolates and are organized into *Enterovirus* and *Rhinovirus* genera as Human Enteroviruses A-D, Poliovirus, *Rhinovirus* A and *Rhinovirus* B according to convention as provided by the International Committee on Taxonomy of Viruses (ICTV). The target sequences (SEQ ID NOS:1-6) are in the Sequence Listing table at the end of the specification.

An important feature of the present invention is the high degree of sequence conservation between viruses in the two genera, *Enterovirus* and *Rhinovirus*, as shown in FIG. 3. The prototypic member of the Picornaviridae family is poliovirus and the targeting sequences (described below) are made in reference to the poliovirus sequence. Table 2 lists the corresponding target regions in a number of clinically relevant Enteroviruses (*Enterovirus* Surveillance—United States, 200-2001. MMWR 2002; 51:1047-1049) and *Rhinoviruses*. The target homologies for the target region is shown in FIG. 3. The target sequence identified as SEQ ID NO:7 represents a combined target sequence, where the letter "Y" in the sequence represents a pyrimidine base, i.e., may be either C or T in SEQ ID NOS:1-6.

Targeting sequences are designed to hybridize to a region of the target sequence as listed in Table 3. Selected targeting sequences can be made shorter, e.g., 12 bases, or longer, e.g., 40 bases, and include a small number of mismatches, as long as the sequence is sufficiently complementary to hybridize with the target, and forms with the virus positive-strand, a heteroduplex having a Tm of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

TABLE 2

Exemplary Human Picornavirus Nucleic Acid Target Sequences

| Virus | Ref. No. | GB No. | Region | SEQ ID NO |
|---|---|---|---|---|
| | 5'–32 Nucleotide Target Region | | | |
| Poliovirus-Mahoney strain | NC 002058 | V01149 | 443–474 | 1 |
| Enterovirus A (CV-A16) | NC 001612 | U05876 | 452–483 | 1 |
| Enterovirus 71 (HEV-71) | | U22521 | 448–479 | 2 |
| Enterovirus B (CV-B1) | NC 001472 | M16560 | 446–477 | 2 |
| Coxsackievirus B3 (CV-B3) | | M88483 | 447–478 | 2 |
| Coxsackievirus B2 (CV-B2) | | AF081485 | 448–479 | 2 |

TABLE 2-continued

Exemplary Human Picornavirus Nucleic Acid Target Sequences

| Virus | Ref. No. | GB No. | Region | SEQ ID NO |
|---|---|---|---|---|
| | 5'–32 Nucleotide Target Region | | | |
| Coxsackievirus B4 (CV-B4) | | X05690 | 448–479 | 2 |
| Coxsackievirus B5 (CV-B5) | | X67706 | 448–479 | 2 |
| Coxsackievirus A9 (CV-A9) | | D00627 | 448–479 | 1 |
| Echovirus 4 (EV-4) | | X89534 | 331–362 | 2 |
| Echovirus 6 (EV-6) | | U16283 | 446–477 | 3 |
| Echovirus 11 (EV-11) | | X80059 | 449–480 | 4 |
| Echovirus 13 (EV-13) | | AF412361 | 259–290 | 2 |
| Echovirus 18 (EV-18) | | AF412366 | 259–290 | 2 |
| Echovirus 25 (EV-25) | | AY302549 | 466–477 | 4 |
| Enterovirus C (CV-A21) | NC 001428 | D00538 | 441–472 | 2 |
| Enterovirus D (HEV-70) | NC 001430 | D00820 | 446–477 | 1 |
| Rhinovirus A (HRV-89) | NC 001617 | M16248 | 442–473 | 5 |
| Rhinovirus B (HRV-14) | NC 001490 | K02121 | 453–484 | 6 |

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The oligomer may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability. An example of this is shown in Table 3 below wherein the 5'-32b antisense targeting oligomer (SEQ ID NO:9) has guanine incorporated at positions 7 and 10 compared to the 5'-32a antisense targeting oligomer that has adenine residues at these positions. Comparison of the 5'-32b sequence with the 5'-32 target sequences (SEQ ID NOS:1-6), demonstrates the broad range of complementarity that C/U:G base pairing provides. Specifically, guanine residues at positions 4, 5, 7, 11 and 14 in the 5'-32b targeting oligomer provide complete complementarity across the all the picornavirus 5'-32 target sequences (SEQ ID NOS:1-6) listed in Table 2. Although the target sequences shown in FIG. 3 and listed in Table 2 contain T for thymidine, which is the convention for sequence listings, it will be appreciated that because picornaviruses are RNA viruses, the T residues refer to uracil.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol*. Vol. 154 pp. 94-107. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

The antisense activity of the oligomer may be enhanced by using a mixture of uncharged and cationic phosphorodiamidate linkages as shown in FIGS. 2G and 2H. The total number of cationic linkages in the oligomer can vary from 1 to 10, and be interspersed throughout the oligomer. Preferably, the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Table 3 below shows exemplary targeting sequences, in a 5'-to-3' orientation, that are complementary to a broad spectrum of picornaviruses, specifically members of the *Enterovirus* and *Rhinovirus* genera. The targeting sequences listed below in Table 3 provide a collection of targeting sequences from which targeting sequences may be selected, according to the general class rules discussed above. As seen, the targeting sequences represented by SEQ ID NOS: 8 and 9 can be represented by SEQ ID NO:10, where "R" represents a purine, either A or G.

TABLE 3

Exemplary Antisense Oligomer Targeting Sequences

| PMO | Target Nucleotides | GenBank Acc. No. | Targeting Antisense Oligomer (5' to 3') | SEQ ID NO. |
|---|---|---|---|---|
| 5'-32a | 443-474 | V00149 | GTTGGGATTAGCCGCATTCAGG GGCCGGAGGA | 8 |
| 5'-32b | 443-474 | V00149 | GTTGGGGTTGGCCGCATTCAGG GGCCGGAGGA | 9 |
| 5'-32 | 443-474 | | GTTGGGRTTRGCCGCATTCAGG GGCCGGAGGA | 10 |

TABLE 3-continued

Exemplary Antisense Oligomer Targeting Sequences

| PMO | Target Nucleotides | GenBank Acc. No. | Targeting Antisense Oligomer (5' to 3') | SEQ ID NO. |
|---|---|---|---|---|
| PV444 | 444-463 | V00149 | CCGCATTCAGGGGCCGGAGG | 11 |
| PV449 | 449-470 | V00149 | GGATTAGCCGCATTCAGGGGCC | 12 |
| PV454 | 454-474 | V00149 | GTTGGGATTAGCCGCATTCAG | 13 |

III. Antisense Oligonucleotide Analog Compounds

A. Properties

As detailed above, the antisense oligonucleotide analog compound (the term "antisense" indicates that the compound is targeted against the virus' positive-sense strand RNA) has a base sequence targeting a region that includes one or more of the following; 1) the 5' untranslated region of the positive sense viral RNA and; 2) the internal ribosome entry site within the 5' untranslated region. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenylalanine, cysteine, beta-alanine and 6-aminohexanoic acid. Exemplary arginine-rich delivery peptides are described in the Sequence Listing table as SEQ ID NOS:14-19. The use of arginine-rich peptide-PMO conjugates can be used to enhance cellular uptake of the antisense oligomer (See, e.g. Moulton, Nelson et al. 2004; Nelson, Stein et al. 2005).

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNaseH

Two general mechanisms have been proposed to account for inhibition of expression by antisense oligonucleotides. (See e.g., (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme et al., 1996), morpholino oligonucleotides, peptide nucleic acids (PNA's), certain 2'-O-allyl or 2'-O-alkyl modified oligonucleotides (Bonham, 1995), and N3'-P5' phosphoramidates (Gee, 1998; Ding, 1996).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent applications, Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of picornavirus RNA, as described above) the method can be used to detect the presence of a given picornavirus virus, or reduction in the amount of virus during a treatment method.

E. Exemplary Oligomer Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine, thymidine and uracil. Suitable backbone structures include carbonate (2A, R=O) and carbamate (2A, R=$NH_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, $R_1$, $R_2$=$CH_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F. Also shown is a cationic linkage in FIG. 2H wherein the nitrogen pendant to the phosphate atom in the linkage of FIG. 2G is replaced with a 1-piperazino structure. The method for synthesizing the 1-piperazino group linkages is described below with respect to FIG. 5. FIG. 2H is an example of a cationic linkage group.

As noted above, the substantially uncharged oligomer may advantageously include a limited number of charged backbone linkages. One example of a cationic charged phosphordiamidate linkage is shown in FIG. 2H. This linkage, in which the dimethylamino group shown in FIG. 2G is replaced by a 1-piperazino group as shown in FIG. 2H, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217, 866, 5,142,047, 5,034,506, 5,166,315, 5,185, 444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the α-morpholino subunit types are also shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
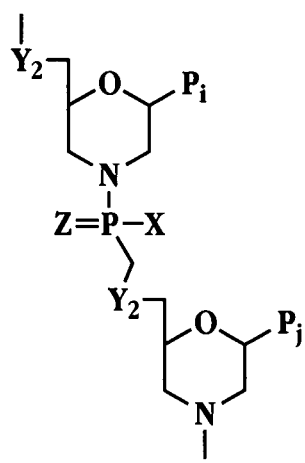
Figure 1D:
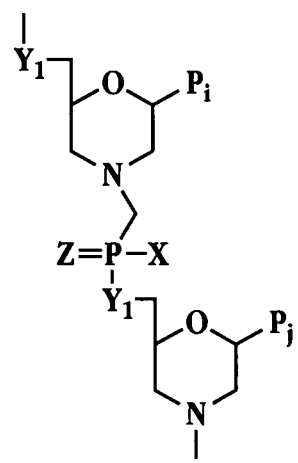

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where X=$NH_2$ or N($CH_3$)$_2$, Y=O, and Z=O and in FIG. 2G.

As noted above, the substantially uncharged oligomer may advantageously include a limited number of charged backbone linkages. One example of a cationic charged phosphordiamidate linkage is shown in FIG. 2H. This linkage, in which the dimethylamino group shown in FIG. 2G is replaced by a 1-piperazino group as shown in FIG. 2H, can be substituted for any linkage(s) in the oligomer. By including between two to eight such cationic linkages, and more generally, at least two and no more than about half the total number of linkages interspersed along the backbone of the otherwise uncharged oligomer, antisense activity can be enhanced without a significant loss of specificity. The charged linkages are preferably separated in the backbone by at least 1 and preferably 2 or more uncharged linkages.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Picornavirus Viral Replication

The antisense compounds detailed above are useful in inhibiting replication of single-stranded, positive-sense RNA viruses of the Picornaviridae family. In one embodiment, such inhibition is effective in treating infection of a host animal by these viruses. Accordingly, the method comprises, in one embodiment, exposing a mammalian cell infected with the virus with an oligonucleotide antisense compound effective to inhibit the replication of the specific virus. In this embodiment, the cells are exposed to the compound either in vitro or in vivo, where the method is used in the latter case to treat a mammalian subject, e.g., human or domestic animal, infected with a given virus. It is contemplated that the antisense oligonucleotide arrests the growth of the RNA virus in the host. The RNA virus may be decreased in number or eliminated with little or no detrimental effect on the normal growth or development of the host.

In the present invention as described in the Examples, Phosphorodiamidate Morpholino Oligomers (PMOs), designed to hybridize to specific regions of the poliovirus 5' UTR, are evaluated for their ability to inhibit IRES-mediated translation in a cell-free translation system. The region of the virus 5' UTR noted above having the target region is highly conserved within the Picornaviridae family and even more highly conserved within the *Enterovirus* and *Rhinovirus* genera that are specifically targeted. The PMO described herein will target most, if not all, picornavirus virus species because of the high degree of homology between viral species at the respective targets (SEQ ID NOS:1-6) as shown in FIG. 3.

A. Identification of the Infective Agent

The specific virus causing the infection can be determined by methods known in the art, e.g. serological, genotyping, or cultural methods, or by methods employing the antisense oligomers of the present invention.

Serological identification employs a viral sample or culture isolated from a biological specimen, e.g., stool, urine, cerebrospinal fluid, blood, nasopharyngeal secretions, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Genotyping methods include polymerase chain reaction (PCR) methods using genotype-specific primers or genomic sequencing of viral nucleic acid obtained from the infected individual.

Another method for identifying the viral infective agent in an infected subject employs one or more antisense oligomers targeting broad families and/or genera of viruses. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligomer into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). As described above, the use of arginine-rich cellular delivery peptides conjugated to the antisense oligomer may also be used. Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter;

or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc., and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml of less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

V. Examples

The following examples illustrate but are not intended in any way to limit the invention.

A. Materials and Methods

Standard recombinant DNA techniques are employed in all constructions, as described in Ausubel, F M et al., in CURRENT PROTOCOLS IN MOLECULAR BIOLOGY, John Wiley and Sons, Inc., Media, Pa., 1992 and Sambrook, J. et al., in MOLECULAR CLONING: A LABORATORY MANUAL, Cold Spring Harbor Laboratory Press, Cold Spring Harbor, N.Y., Vol. 2, 1989).

All peptides are custom synthesized by Global Peptide Services (Ft. Collins, Co.) or at AVI BioPharma (Corvallis, Oreg.) and purified to >90% purity. Phosphorodiamidate morpholino oligomers (PMOs) are synthesized at AVI BioPharma in accordance with known methods, as described, for example, in (Summerton and Weller 1997) and U.S. Pat. No. 5,185,444.

For Examples 2 and 3 described below, PMO oligomers are conjugated at the 5' end with an arginine-rich peptide $(RXR)_4$ XB-PMO (where R is arginine, X is 6-aminohexanoic acid and B is beta-alanine) to enhance cellular uptake as described (U.S. patent application 60/466,703 and Moulton, Nelson et al. 2004; Nelson, Stein et al. 2005). This peptide is also called P007 and listed as SEQ ID NO:13 in the Sequence Listing table.

Preparation of Morpholino Oligomers Having Cationic Linkages

Figure 5:
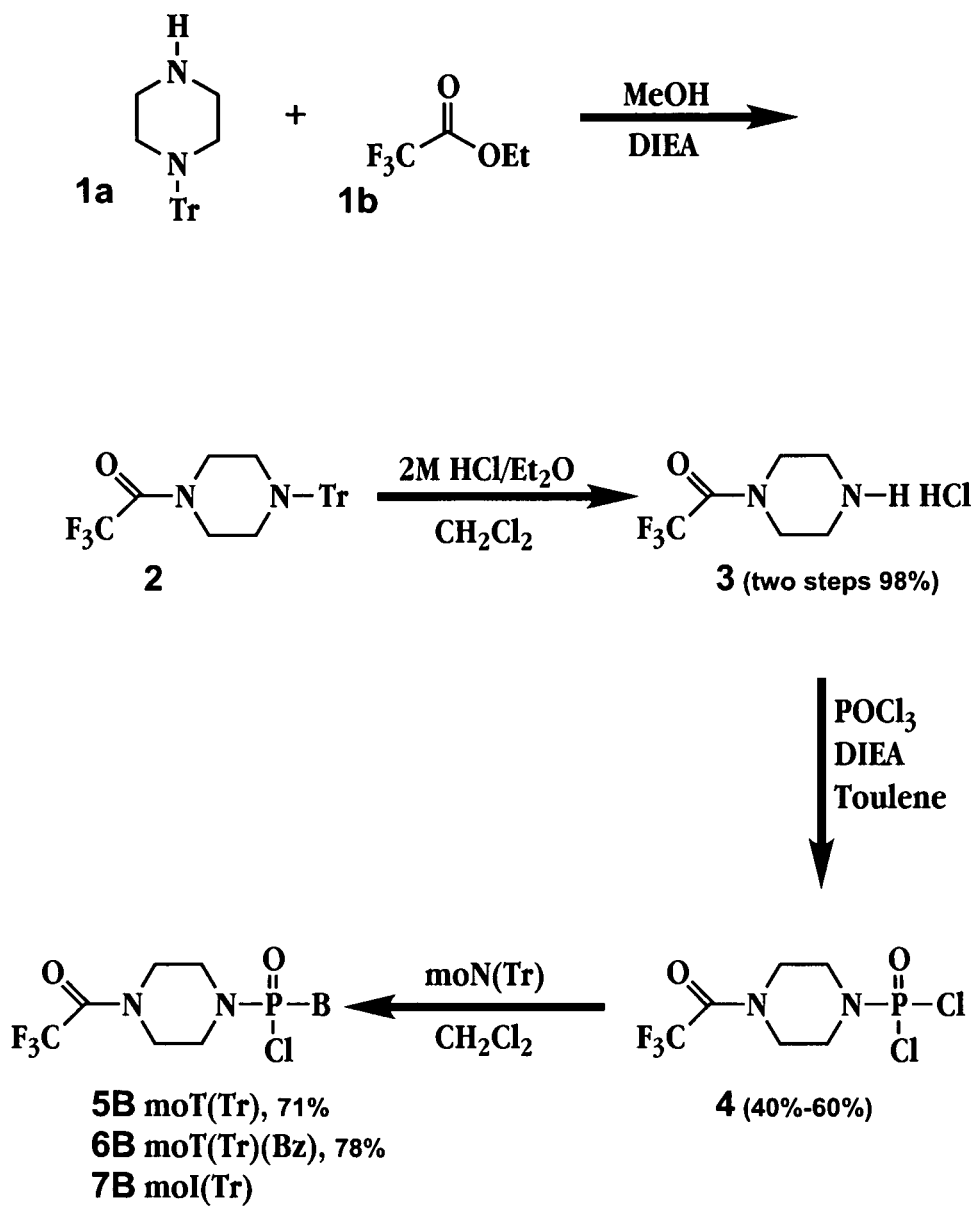
FIG. 5 shows the synthetic steps to produce subunits used to produce +PMO containing the (1-piperazino) phosphinylideneoxy cationic linkage as shown in FIG. 2H.

A schematic of a synthetic pathway that can be used to make morpholino subunits containing a (1 piperazino) phosphinylideneoxy linkage is shown in FIG. 5; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5, 6, 7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

Example 1

Figure 4:
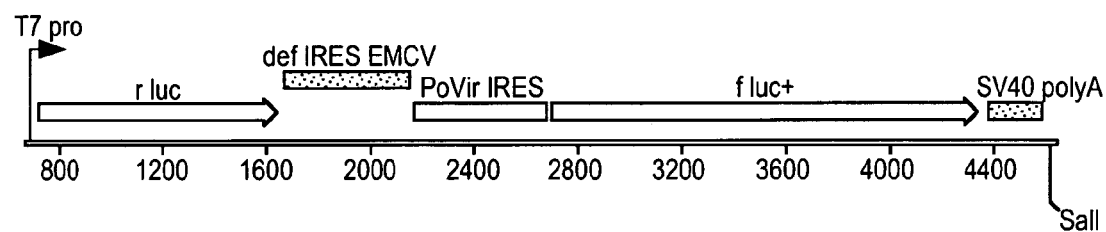
FIG. 4 shows a genetic map of the dual luciferase reporter construct pR&Fluc-PolioIRES.

Inhibition of Picornavirus Virus RNA Translation with Phosphorodiamidate Morpholino Oligomers Phosphorodiamidate Morpholino Oligomers (PMOs), designed to hybridize to a specific region of the poliovirus internal ribosome entry site (IRES) region of poliovirus, as described above, are evaluated for their ability to inhibit translation in a rabbit reticulcyte lysate (RRL) assay. A dual reporter expression plasmid construct is derived as follows. A 507 nucleotide fragment of the 5' untranslated region of the poliovirus genome (ncts 124 to 630, GenBank No. V01149) is synthesized (BlueHeron, Inc) and inserted into the intercistronic region of a dual luciferase reporter plasmid described previously (Johannes, Carter et al. 1999; Wilson, Powell et al. 2000; Brasey, Lopez-Lastra et al. 2003) and named herein as pR&Fluc. The resulting plasmid, pR&Fluc-PolioIRES is shown schematically in FIG. 4. For transcription in vitro, the dicistronic luciferase pR&Fluc-PolioIRES construct is digested with BamHI and linear DNA is transcribed with T7 RNA polymerase using the RiboMAX protocol (Promega, Inc) to produce rLuc/fLuc RNA. Uncapped dicistronic RNAs are translated in the RRL, as recommended, and products of translation reactions are measured enzymatically using the dual luciferase reporter assay system (Promega).

Figure 6A:
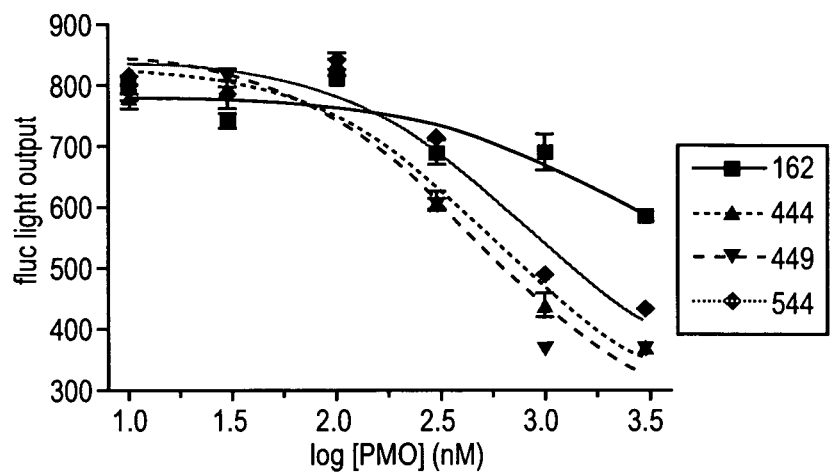
FIGS. 6A and 6B show results of cell-free translation assays using exemplary antisense compounds of the invention and their associated EC50 concentrations.
Figure 6B:
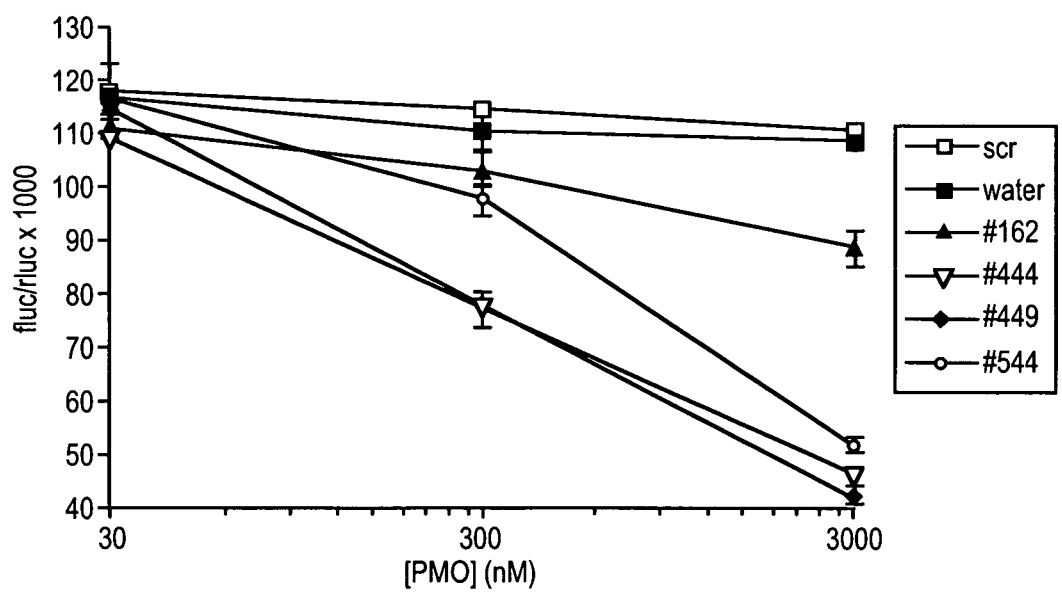

Prior to cell-free translation, one nanomolar of the dicistronic RNA is incubated with PMOs (SEQ ID NOS: 11-13) at varying concentrations ranging from 0.01 to 10 micromolar. Relative inhibition of the fLuc downstream reporter gene is measured using a fluorometer. FIG. 6A shows the fLuc light output from rLuc/fLuc RNA in the presence of four different PMOs including two that are examples of the present invention, 444 and 449; SEQ ID NOS: 11 and 12, respectively. These two PMOs are compared to two other PMOs, 162 and 544, which are targeted to regions of the poliovirus IRES approximately 280 bases in the 5' direction and 100 bases in the 3' direction, respectively. The sequence of PMO 162 is SEQ ID NO:20 and for PMO 544 it is SEQ ID NO:21. The effective concentrations at which 50% inhibition (EC50) of fLuc output are also listed in FIG. 6. Both the 444 and 449 PMOs have significantly lower EC50s than either of the comparator PMOs. FIG. 6B shows similar results to FIG. 6A but the data shown is the fLuc to rLuc signal ratio which normalizes the results to the rLuc internal control. The region targeted by the 544 PMO is equally conserved across the Picornaviridae family (See U.S. Provisional Patent Application 60/715,888) as compared to the region targeted by the 444 and 449 PMOs, the focus of the present invention. However, the latter PMOs demonstrate EC50s in this assay that are as much as 45% lower than those observed with the 544 PMO.

Example 2

Inhibition of Coxsackievirus B3 (CVB3) in Tissue Culture with PMOs that Target the 5' UTR of CVB3

The antiviral activity of CVB3-specific PMOs is determined by measuring viral protein expression in PMO-treated, CVB3-infected cells. The test is performed on either cardiomyocytes (HL-1 cells) or HeLa cells. Cell monolayers (6-well plates) are seeded 16 to 20 hours prior to treatment with PMO or infection with virus. Serum-containing medium is replaced with serum-free medium during PMO treatment and infection. The infection is allowed to proceed for either 7 h or 24 h at 37° C. prior to collection of cells and the preparation of cell lysates for immunoblot detection of viral capsid protein by Western blot (i.e. immunoblot) assay using a polyclonal antibody to the CVB3 VP1 gene. Antisera against beta-actin is included as a loading control.

In one set of experiments, $6 \times 10^5$ HL-1 cells (cardiomyocytes) are seeded in 6-well plates for 16-20 h. Culture medium is then replaced with serum-free medium and incubated with individual PMOs at final concentration of 10 µM. Four hours post-infection, cells are infected with CVB3 at a multiplicity of infection (MOI) of 10. At 24 hours post-infection, cell lysates are collected for Western immunoblot analysis to detect viral capsid protein VP1. Immunological detection of beta-actin is used as a loading control. Eight different peptide (P007)-conjugated PMOs are tested.

One of the effective antisense PMOs (PV444, PV449, or PV454; SEQ ID NOS:11, 12, and 13) is selected for a dose response assay using HeLa cells under the same conditions as described above. The concentration range analyzed is from 0.01 to 20 micromolar PMO. An estimated effective concentration sufficient for a reduction in viral replication of 50% ($EC_{50}$) for this PMO is between 5 and 10 micromolar.

Effective inhibition of CVB3 replication with two PMOs is observed as described above. This inhibition is under conditions where the PMO is introduced four hours prior to infection.

Example 3

Inhibition of CVB3-Induced Cytopathic Effects in Tissue Culture with PMOs that Target the 5' UTR of CVB3

Another measure of antiviral activity is to observe a reduction in cytopathic effects (CPE) in tissue culture experiments. Three P007-conjugated PMO are selected for these analyses, PV444, PV449, and PV454 (SEQ ID NOS:11, 12, and 13, respectively) are used to treat both HL-1 cells (cardiomyocytes) and HeLa cells under the same conditions described in Example 2 above. Four hours post-treatment with PMO, cells are infected with CVB3 at an MOI of ten. Photomicrographs are taken 24 hours post-infection for HeLa cells.

The invention claimed is:

1. A method of treating viral infection of mammalian cells by an *Enterovirus* or *Rhinovirus*, comprising exposing host cells to an effective amount of an antiviral compound that comprises a morpholino antisense oligonucleotide of between 15 and 25 morpholino subunits having a substantially uncharged, nuclease-resistant backbone containing phosphorodiamidate intersubunit linkages joining a morpholino nitrogen of one subunit to a 5' exocyclic carbon of an adjacent subunit, wherein the morpholino antisense oligonucleotide comprises a targeting sequence of at least 15 nucleotide bases complementary to SEQ ID NO:7 and, conjugated to the morpholino antisense oligonucleotide, an arginine-rich polypeptide effective to promote uptake of the antiviral compound into the host cells, wherein the arginine-rich polypeptide has the sequence of SEQ ID NO:15.

2. The method of claim 1, wherein the morpholino antisense oligonucleotide forms a heteroduplex with its target sequence, wherein the heteroduplex has a $T_m$ of at least 45° C.

3. The method of claim 1, wherein the morpholino antisense oligonucleotide contains an intersubunit linkages in accordance with the structure:

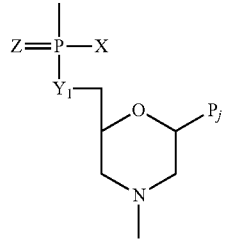

wherein $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino, or —$NR_2$, where each R is independently hydrogen or methyl.

4. The method of claim 1, wherein the morpholino antisense oligonucleotide contains an intersubunit linkages in accordance with the structure:

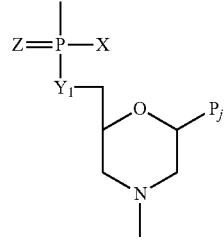

wherein $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino, —$NR_2$, where each R is independently hydrogen or methyl, or 1-piperazine, wherein at least 2 and no more than half of the total number of intersubunit linkages are 1-piperazine.

5. The method of claim 1, wherein the oligonucleotide has at least 15 nucleotide bases contained in SEQ ID NO:10.

6. The method of claim 5, wherein the oligonucleotide is selected from the group consisting of SEQ ID NOS:11, 12, and 13.

7. The method of claim 1, wherein the exposing is by administering to a subject a therapeutically effective amount of the antiviral compound.

8. The method of claim 7, further comprising administering a second antiviral compound to the subject.

* * * * *

UNITED STATES PATENT AND TRADEMARK OFFICE
CERTIFICATE OF CORRECTION

| | |
|---|---|
| PATENT NO. | : 8,524,676 B2 |
| APPLICATION NO. | : 11/517757 |
| DATED | : September 3, 2013 |
| INVENTOR(S) | : David A. Stein et al. |

It is certified that error appears in the above-identified patent and that said Letters Patent is hereby corrected as shown below:

Title Page 2, Column 2, Item (56):
"Linkletter, B. A. and Bruice, T.C., "Solid-phase synthesis of positively charged deoxynucleic guanidine (DNG) modified oligoriucleotidos containing neutral urea linkages: Effect of charge deletions on binding and fidelity." *Biorg. Med. Chem.* 8(11): 1893-1901 (2000)." should read, --Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Biorg. Med. Chem.* 8(11): 1893-1901 (2000).--.

Title Page 3, Column 1, Item (56):
"Anderson et al , "Inhibition of Human Cytomegalovirus Immediate-Early Gene Expression by an Antisense Oligonucleotide Complementary to Immediate-Early RNA" Antimicrobial Agents and Chemotherapy 40(9): 2004-2011, 1996." should read, --Anderson et al., "Inhibition of Human Cytomegalovirus Immediate-Early Gene Expression by an Antisense Oligonucleotide Complementary to Immediate-Early RNA" Antimicrobial Agents and Chemotherapy 40(9): 2004-2011, 1996.--.

Title Page 3, Column 1, Item (56):
"Deas et al , "Inhibition of Flavivirus Infections by Antisense Oligomers Specifically Suppressing Viral Translation and RNA Replication" Journal of Virology 79(8): 4599-4609, 2005." should read, --Deas et al., "Inhibition of Flavivirus Infections by Antisense Oligomers Specifically Suppressing Viral Translation and RNA Replication" Journal of Virology 79(8): 4599-4609, 2005.--.

Title Page 3, Column 2, Item (56):
"GenBank Accession no. V01149, "Human poliovirus 1 Mahoney, complete genome" retrieved from http://www.ncbi.nlm.nih.gov/nuc-core/61252, May 12, 2010." should read, --GenBank Accession no. V01149, "Human poliovirus 1 Mahoney, complete genome" retrieved from http://www.ncbi.nlm.nih.gov/nuccore/61252, May 12, 2010.--.

Signed and Sealed this
Twenty-fifth Day of March, 2014

Michelle K. Lee
*Deputy Director of the United States Patent and Trademark Office*

CERTIFICATE OF CORRECTION (continued)
U.S. Pat. No. 8,524,676 B2

Title Page 3, Column 2, Item (56):
"Kinney et al , "Inhibition of Dengue Virus Serotypes 1 to 4 in Vero Cell Cultures with Morpholino Oligomers" Journal of Virology 79(8): 5116-5128, 2005." should read, --Kinney et al., "Inhibition of Dengue Virus Serotypes 1 to 4 in Vero Cell Cultures with Morpholino Oligomers" Journal of Virology 79(8): 5116-5128, 2005.--.

Title Page 3, Column 2, Item (56):
"Raviprakash et al , "Inhibition of Dengue Virus by Novel, Modified Antisense Oligonucleotides" Journal of Virology 69(1): 67-74, 1995." should read, --Raviprakash et al., "Inhibition of Dengue Virus by Novel, Modified Antisense Oligonucleotides" Journal of Virology 69(1): 67-74, 1995.--.

In the Claims:

Column 31, Lines 28-29:
"3. The method of claim 1, wherein the morpholino antisense oligonucleotide contains an intersubunit linkages in" should read, --3. The method of claim 1, wherein the morpholino antisense oligonucleotide contains an intersubunit linkage in--.

Column 32, Lines 11-12:
"4. The method of claim 1, wherein the morpholino antisense oligonucleotide contains an intersubunit linkages in" should read, --4. The method of claim 1, wherein the morpholino antisense oligonucleotide contains an intersubunit linkage in--.